United States Patent
Respini et al.

(10) Patent No.: US 10,591,396 B2
(45) Date of Patent: *Mar. 17, 2020

(54) METHOD OF DETERMINING THE STABILITY RESERVE AND SOLUBILITY PARAMETERS OF A PROCESS STREAM CONTAINING ASPHALTENES BY JOINT USE OF TURBIDIMETRIC METHOD AND REFRACTIVE INDEX

(71) Applicant: BAKER HUGHES, A GE COMPANY, LLC, Houston, TX (US)

(72) Inventors: Marco Respini, Casalmorano (IT); Giuseppe Della Sala, Liverpool (GB); Corina Sandu, Pearland, TX (US); Gavin Mark Medine, Amsterdam (NL); Sai Reddy Pinappu, Houston, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/424,290

(22) Filed: Feb. 3, 2017

(65) Prior Publication Data

US 2017/0227433 A1    Aug. 10, 2017

Related U.S. Application Data

(60) Provisional application No. 62/292,010, filed on Feb. 5, 2016.

(51) Int. Cl.
*G01N 13/00* (2006.01)
*G01N 33/28* (2006.01)
(Continued)

(52) U.S. Cl.
CPC .......... *G01N 13/00* (2013.01); *G01N 21/41* (2013.01); *G01N 21/4133* (2013.01);
(Continued)

(58) Field of Classification Search
CPC ............ G01N 13/00; G01N 21/4133; G01N 2021/4153
See application file for complete search history.

(56) References Cited

U.S. PATENT DOCUMENTS 5,871,634 A * 2/1999 Wiehe .................. C10G 9/005
208/48 R
9,127,213 B2 * 9/2015 Komalarajun ....... C10G 21/003
(Continued)

FOREIGN PATENT DOCUMENTS

CA    3013591    8/2017
EP    3147649    3/2017
(Continued)

OTHER PUBLICATIONS

European Patent Office; PCT International Search Report, Issued in Connection to PCT/US2017/016493; dated Jul. 24, 2017; 6 pages; Europe.
(Continued)

*Primary Examiner* — Christine A Enad
(74) *Attorney, Agent, or Firm* — Greenberg Traurig LLP

(57) ABSTRACT

A method is provided for determining the solubility parameters for a process stream via the joint use of turbidimetric detection of asphaltenes flocculation, which is used to determine and detect the onset flocculation of asphaltenes of the process stream, and a refractive index to determine the process stream solubility parameters such as the solubility blending number and insolubility number.

14 Claims, 1 Drawing Sheet

(51) Int. Cl.
*G01N 21/41* (2006.01)
*G01N 21/83* (2006.01)

(52) U.S. Cl.
CPC ............. *G01N 21/83* (2013.01); *G01N 33/28* (2013.01); *G01N 33/2823* (2013.01); *G01N 2201/12* (2013.01)

(56) References Cited

U.S. PATENT DOCUMENTS

| | | | |
|---|---|---|---|
| 9,921,203 B2* | 3/2018 | Rogel | G01N 33/2823 |
| 2002/0140925 A1 | 10/2002 | Mougin | |
| 2004/0012782 A1* | 1/2004 | Mason | G01N 21/51 356/338 |
| 2009/0032435 A1* | 2/2009 | Brons | C10G 9/16 208/14 |
| 2010/0122939 A1* | 5/2010 | Bauer | C10G 47/26 208/425 |
| 2012/0125087 A1* | 5/2012 | Sandu | G01N 21/8507 73/64.55 |
| 2013/0026074 A1 | 1/2013 | Koseoglu et al. | |
| 2013/0098735 A1* | 4/2013 | Corscadden | C10G 55/04 196/14.52 |
| 2013/0124106 A1* | 5/2013 | Rogel | G01N 33/2823 702/25 |
| 2013/0161233 A1* | 6/2013 | Bennett | C10G 31/00 208/14 |
| 2013/0341241 A1* | 12/2013 | Respini | G01N 21/41 208/14 |
| 2014/0209714 A1* | 7/2014 | Hassan | B02C 23/08 241/15 |
| 2014/0275663 A1* | 9/2014 | Brons | C08F 8/32 585/3 |
| 2015/0152338 A1 | 6/2015 | Respini et al. | |
| 2015/0160110 A1* | 6/2015 | Aquino Olivos | G01N 9/36 73/53.05 |
| 2015/0219614 A1 | 8/2015 | Respini et al. | |
| 2016/0097757 A1* | 4/2016 | Sieben | G01N 1/28 436/60 |
| 2016/0122667 A1* | 5/2016 | Evans | C10G 9/36 208/70 |
| 2016/0216191 A1 | 7/2016 | Balashanmugam et al. | |
| 2017/0082539 A1 | 3/2017 | Respini et al. | |
| 2017/0115266 A1 | 4/2017 | Ratulowski et al. | |
| 2017/0227434 A1 | 8/2017 | Respini et al. | |

FOREIGN PATENT DOCUMENTS

| | | |
|---|---|---|
| WO | 2013/070412 A1 | 5/2013 |
| WO | 2017/136716 | 8/2017 |
| WO | 2018/195543 | 10/2018 |

OTHER PUBLICATIONS

European Patent Office; PCT Written Opinion of the International Searching Authority, Issued in Connection to PCT/US2017/016493; dated Jul. 24, 2017; 10 pages; Europe.

European Patent Office; PCT International Search Report, Issued in Connection to PCT/US2018/028909; dated Aug. 10, 2018; 7 pages; Europe.

European Patent Office; PCT Written Opinion of the International Searching Authority , Issued in Connection to PCT/US2018/028909; dated Aug. 10, 2018; 11 pages; Europe.

European Patent Office; Annex to Communication Relating to the Results of the Partial International Search, issued in connection to PCT/US18/28909; dated Aug. 7, 2018; 8 pages; Europe.

Patent Coopration Treaty; PCT International Preliminary Report on Patentability, issued in connection to PCT/US17/016493; dated Aug. 7, 2018; 9 pages; Switzerland.

J. Buckley, J. Wang Procedure for Measuring the Onset of Asphaltenes Flocculation, PRRC 01-18 methods ASTM D-7157.

European Patent Office; Communication Pursuant to Rule 161(1) and 162 EPC, issued in connection to EP17706052.2; 3 pages; Europe.

Standard Test Method for Determination of Intrinsic Stability of Asphaltene-Contining Residues, Heavy Fuel Oils, and Crude Oils (n-Heptane Phase Separation; Optical Detection); D7157-12; ASTM International; Apr. 3, 2019; 9 pages.

* cited by examiner

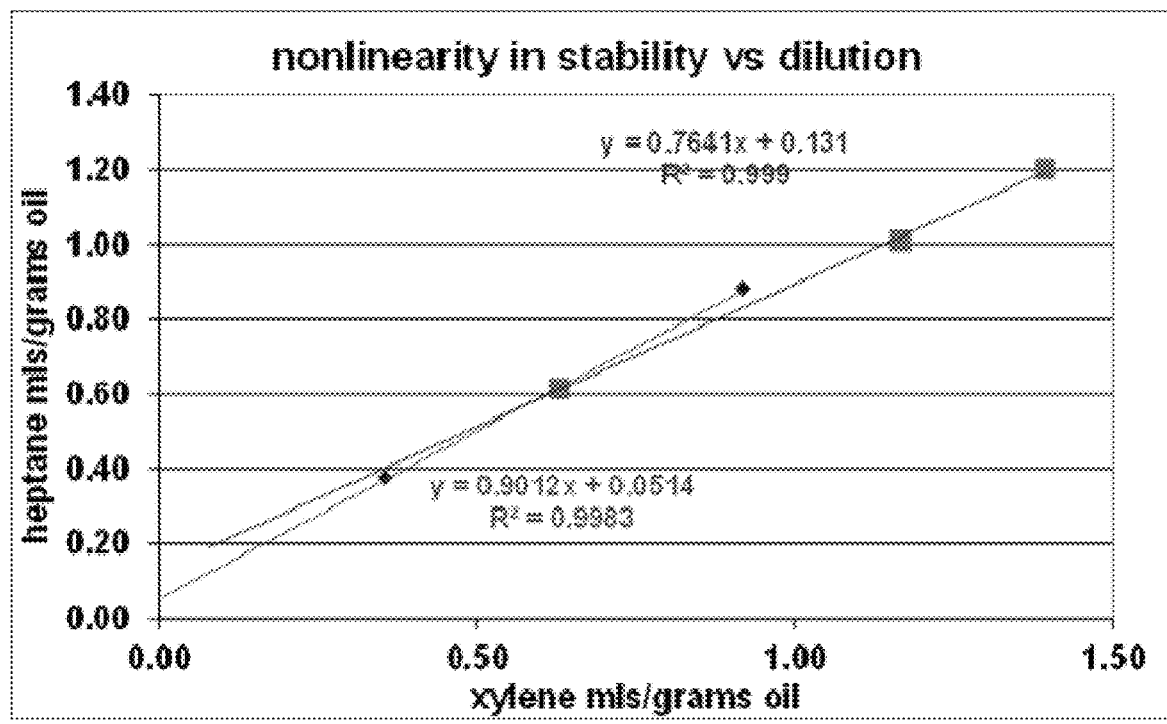

METHOD OF DETERMINING THE STABILITY RESERVE AND SOLUBILITY PARAMETERS OF A PROCESS STREAM CONTAINING ASPHALTENES BY JOINT USE OF TURBIDIMETRIC METHOD AND REFRACTIVE INDEX

RELATED APPLICATIONS

This application claims the benefit, and priority benefit, of U.S. Application Ser. No. 62/292,010, filed Feb. 5, 2016, the disclosure and contents of which are incorporated by reference herein in its entirety.

BACKGROUND

Field of the Invention

It is known in the art that solubility parameters of streams containing asphaltenes are related to the capability of the oil matrix to disperse/solvate asphaltenes and the tendency of asphaltenes to precipitate from the stream solvating them. Solubility parameters are a thermodynamic quantity related to cohesive energy and widely applied to determine solubilities of compounds in solvents. These solubility parameters are often respectively reported as a solubility blending number (related to the stream solubility parameter) and an insolubility number (solubility parameter of the asphaltenes in the stream).

The classic techniques reported in literature for the determination of the solubility parameters are inaccurate and their applicability is limited. For example, these traditional methods are limited and not as accurate to certain types of streams such as light crude oils with a low asphaltene content and heavy refinery residuals (thermally cracked or hydrocracked). They are also limited and not accurate for determining the impact of fluxants such as refinery distillates on the change of the matrix solubility parameters on these particular streams.

The refractive index can be utilized to measure the oil solubility parameter and calculate the solubility blending number starting from proprietary correlations based on experimental data. This method gives an approximate estimate of the stability reserve of asphaltenes in crude oils. However, the refractive index alone, without any other measurement, cannot give a direct and accurate estimation of the stability of thermally cracked streams such as FCC slurries, Eni slurry Technology unit (EST), HOil, LC finers and visbreakers under existing techniques.

Improvements in this field of technology are desired.

SUMMARY

Various illustrative embodiments of a method of determining the solubility parameters and stability reserve of a process stream containing asphaltenes are disclosed herein. In certain illustrative embodiments, the solubility parameters are determined by measuring the refractive index of the process stream, RI and the refractive index at the flocculation onset of the asphaltenes ($RI_o$), wherein the flocculation onset is determined via turbidimetric titration. The refractive index parameter at the flocculation onset, $RI_o$ can be utilized as a direct measurement of the insolubility number, IN. The refractive index parameter of the stream containing asphaltenes, RI, can be utilized as a direct measurement of the solubility blending number, $SB_o$. The stability reserve can be determined from the solubility blending number and the insolubility number ($SB_o$/IN).

The measurements can include recovering precipitated asphaltenes at the flocculation onset, redispersing the precipitated asphaltenes in a solvent to form an asphaltenic solution, and measuring the refractive index parameters of the asphaltenic solution ($RI_a$). The refractive index parameters can be converted into a solubility blending number ($SB_a$) of the precipitated asphaltenes.

In certain aspects, the stability reserve can be the ratio of the solubility blending number to the insolubility number. The precipitated asphaltenes can be recovered via one or more of filtration or centrifugation. The recovered precipitated asphaltenes can be washed with precipitant and then recovered again via one or more of filtration or centrifugation. The precipitated asphaltenes can be redispersed in the solvent at a ratio in the range from 1:1 solvent/asphaltenes to 10:1 solvent/asphaltenes. The process stream can include one or more of light crude oil, heavy crude oil and a refinery stream from the group comprising desalted crudes, vacuum tower bottoms, FCC slurries and heavy fuels. The process stream can include a crude oil derivative from a refinery process. The process stream can include a light crude oil with an asphaltene content of 0.4% or greater. The process stream can include one or more residual thermal cracking streams from a refinery process. The residual thermal cracking streams can include FCC slurry, residua fuel oils, H-Oil, Eni Slurry Technology (EST) bottoms units an LC Finer bottoms and/or visbreaker residua. The process stream can include a residual hydrocracking stream from a refinery process. The process stream can include a refinery distillate stream containing no asphaltenes combined with a stream containing asphaltenes.

Various illustrative embodiments of a method of determining the solubility parameters of asphaltenes contained in a process stream are also disclosed herein. In certain illustrative embodiments, precipitated asphaltenes can be recovered from the process stream using a non-solvent at a ratio in the range from 10:1 solvent/process stream volume to 40:1 solvent/process stream volume. The precipitated asphaltenes can be redispersed in an aromatic solvent to form an asphaltenic solution. The refractive index of the asphaltenic solution can be measured ($RI_s$). The refractive index parameter of the solution can be converted into the refractive index parameter of the asphaltenes ($RI_a$). The refractive index of the asphaltenes can be converted into a solubility parameter. The solubility blending number ($SB_a$) of the precipitated asphaltenes can be calculated from this solubility parameter.

Various illustrative embodiments of a method of determining the solubility parameters of a solvating resin in a process stream are also disclosed herein. The solvating resin can be recovered from the process stream using a solvent. The solvating resin can be redispersed in an aromatic solvent to form a resin solution. The refractive index of the resin solution can be measured ($RI_s$). The refractive index parameters of the solution can be converted into the refractive index parameter of the resins ($RI_r$). The refractive index of the resin can be converted into a solubility parameter. The solubility blending number ($SB_r$) can be calculated from this solubility parameter. The result of SBa-IN is indicative of the stabilizing and solvating role of the resins in the fluid on the critical asphaltenes and can be used to recommend optimized chemical programs.

BRIEF DESCRIPTION OF THE DRAWINGS

A better understanding of the presently disclosed subject matter can be obtained when the following detailed description is considered in conjunction with the following drawings, wherein:

FIG. 1 is a graph showing nonlinearity of stability vs. dilution for a Heithaeus p-value three dilutions procedure in connection with the presently disclosed subject matter.

While the presently disclosed subject matter will be described in connection with the preferred embodiment, it will be understood that it is not intended to limit the presently disclosed subject matter to that embodiment. On the contrary, it is intended to cover all alternatives, modifications, and equivalents, as may be included within the spirit and the scope of the presently disclosed subject matter as defined by the appended claims.

DETAILED DESCRIPTION

According to the illustrative embodiments disclosed herein, a method is provided for determining the solubility parameters for a variety of types of process streams, including but not limited to crude oil and crude oil derivatives from refinery processing containing asphaltenes, and distillation products containing no asphaltenes when blended with asphaltene containing streams.

In certain illustrative embodiments, the presently disclosed subject matter takes advantage of the joint use of turbidimetric detection of asphaltenes flocculation, which is used to determine and detect the onset flocculation of asphaltenes of the process stream coupled with the use of a refractive index to determine the process stream solubility parameters (for example, the solubility blending number and insolubility number).

In certain illustrative embodiments, the stability reserve of the asphaltenes can be determined by the ratio of the solubility blending number ("$SB_o$") (the capability to disperse the asphaltenes by the oil matrix surrounding the asphaltenes) to the insolubility number ("IN") (the asphaltenes insolubility). The $SB_o$ and IN can be determined from the refractive index ("RI") measurements.

In certain illustrative embodiments, the refractive index measurements can be performed at the flocculation onset of the asphaltenes when a non-solvent (precipitant) is added. This RI measurement taken at the onset of asphaltene flocculation ($RI_o$) allows one to determine the insolubility number (IN) of asphaltenes for the particular feedstock in a very clear and accurate way, offering improvement when compared to other methods. In some methods, such as optical methods, due to low amount of asphaltenes present in the feedstock subjected to the measurement, the onset flocculation determination may be difficult and inaccurate. By employing RI measurements at the flocculation onset of the asphaltenes, a direct way to determine the critical solubility parameter at which asphaltenes start to aggregate is possible and is a direct measurement of the IN.

The presently disclosed subject matter provides improved reliability and accuracy in determining these solubility parameters and also extends the determination of the solubility parameters to process streams such as light crude oils with low asphaltene content, refinery heavy residuals from thermal cracking and hydrocracking and refinery distillates containing no asphaltenes.

As used herein, the term "process stream" broadly means streams from industrials processes such as tank blending optimization, refinery crude blending, refinery crude units, desalted crude, vacuum bottom towers resids, heavy fuels, coker, visbreakers, or a fluid originating from such streams. In addition, the same methodology or determinations can be performed during tank or terminal blending. Since the RI technology has a higher degree of sensitivity due to its design, it can be leveraged to both very light asphaltenic containing streams as well as heavy and dark feedstocks. Applying refractive index determinations and coupling them with turbidimetric detection of asphaltene flocculation provides practical advantages and allow their use in controlling and detecting the stability reserve either on the bench or online for a variety or a larger pool of feedstocks than conventional methods. In addition, RI measurements are portable and testing is easy to perform. Thus, the presently disclosed subject matter is suitable as a methodology that could be implemented in local/district labs.

In addition, the use of turbidimetric means, such as near infrared laser based determination of the asphaltenes flocculation onset, allows previously known methods (such as Heithaeus p-value) and similar ASTM methods like the D-7112 and D-7157 to be extended to a much wider range of streams having lower content of asphaltenes and with improved accuracy.

In certain illustrative embodiments, the solubility parameter of the process stream containing asphaltenes can be determined by the use of the refractive index, whereby the critical solubility parameter IN (that is, solubility parameter at the asphaltenes flocculation onset) is determined by measurement of the refractive index at the flocculation point $RI_o$ as determined by turbidimetric titration. These are the most critical asphaltenes and are only a portion of the full content of asphaltenes; however, they are the most relevant for fouling and other asphaltene related issues.

In certain illustrative embodiments, when flocculation onset is reached (as identified by the turbidimetric titration) precipitant dosing is stopped and asphaltene aggregation is allowed to continue until completion (as identified by the flat minimum of the flocculation titration after the peak corresponding to precipitation onset). The critical asphaltenes can then be recovered either by filtration (using a filter from 0.2 to 10 microns, preferably 0.45 to 1 micron porosity) or by centrifugation (1000 to 20000 rpm, 1 minute to 1 hour).

The recovered asphaltenes can be then washed with hot precipitant and recovered again by filtration or centrifugation, to eliminate trapped resins, waxes or other co-precipitated impurities. After the separation and washing, the asphaltenes are re-dispersed in a suitable aromatic solvent, typically xylene, in a ratio varying from 1:1 solvent/asphaltenes up to 10:1 solvent/asphaltenes, in certain illustrative embodiments. The refractive index of this asphaltenic solution $RI_a$ is measured and the solubility parameter of critical asphaltenes determined ($SB_a$).

In certain illustrative embodiments, the refractive index can be directly measured during turbidimetric titration by using a fiber optic or miniature refractometer or any other refractometer that can be coupled with the turbidimeter. For example, near infrared may be utilized. The difference in the solubility parameter of the asphaltenes precipitated at the flocculation onset and the solubility parameter of the process stream with precipitant at the flocculation onset ($SB_a$-IN) is indicative of the stabilizing/solvating role of the resins in the fluid on the critical asphaltenes. The solubility parameters can be determined in both cases using the refractive index ($RI_o$ and $RI_a$).

In certain illustrative embodiments, the solubility parameters of the full range of asphaltenes in the fluid (not restricted to the ones that are most critical and precipitate at the flocculation onset) can be determined by precipitating them from the fluid using an excess non-solvent (typically heptane), at ratios ranging from 10:1 to 40:1 heptane/fluid volume:weight. After recovering (via filtration or centrifugation) and washing with non-solvent in order to remove the trapped contaminants (such as resins and waxes), the solubility parameters of the asphaltenes can be measured by dispersing them in an aromatic solvent ($SB_{total-a}$).

The solubility parameters of the solvating resins ($SB_{total-r}$) can be determined in a similar way, for example by separating them from oil by known literature methods, dispersing them in an aromatic solvent after recovery and measuring the refractive index of the solution of the resins in the solvent.

By detecting the difference of $SB_a$-$SB_o$ one can quantify and measure the efficiency and contribution provided by chemical additive programs designed to influence and improve both the $SB_a$ as well as $SB_o$ to have a positive impact on the overall stability reserve of the feed.

The impact of antifoulants (dispersants and asphaltenes inhibitors) on the solvation/stabilization by asphaltenes can also be tested by using the change in solubility parameters measured according to the presently disclosed subject matter. The impact on the overall stability reserve improvement can be refined by detecting and evaluating their influence on both $SB_o$, $SB_a$ and/or $SB_r$.

In certain illustrative embodiments, $SB_o$ and IN are first determined in the field, for example, onsite at a refinery. This information may be sufficient to take action on additive investigation and recommendation. In the event that further and more specific testing is needed (which usually depends on the nature of the analyzed sample), additional laboratory determinations of $SB_a$ and $SB_r$ can be performed. The field determinations of SB and IN can occur by both titration methods and RI determinations. This step can be followed by extension with additional parameters. The additional parameters can include, for example, recovering precipitated asphaltenes at the flocculation onset, redispersing the precipitated asphaltenes in a solvent to form an asphaltenic solution, measuring the refractive index parameters of the asphaltenic solution ($RI_a$), and converting the refractive index parameters ($RI_a$) into a solubility blending number ($SB_a$) of the precipitated asphaltenes. In other illustrative embodiments, SBa and SBr can be routinely measured and introduced into the field procedure.

The presently disclosed subject matter has a number of advantages when compared to prior art methods. For example, the solubility parameters can be determined more accurately. Traditional methods used multiple dilutions of the fluid containing asphaltenes in aromatic solvents at different oil to solvent ratios. This prior procedure can change the solvation layer of the asphaltenes and produce a serious bias in the results. Deviations from the linearity effects induced by dilution of different solvents were observed in the past. By introducing refractive index determinations on the pristine feedstocks with no dilution one allows a more representative determination of the solubility blending numbers as well as permits a user to quantify and assess the impact of chemical additives on the feedstock stability in a more reliable and accurate fashion.

The presently disclosed methods are also highly reliable due to the accuracy of turbidimetric titration in determining the true asphaltene flocculation onset coupled with the direct and accurate determination of the solubility parameters achievable by the use of the refractive index. For example, the reported error for p-value, SBn and IN from refinery experience and from round robin tests is 20% or greater, whereas the error of the presently disclosed methods is less than 2% in certain illustrative embodiments.

Furthermore, the presently disclosed methods are capable of measuring the solubility parameters for process streams with low asphaltene content, down to about 0.4% asphaltene which is not achievable with current existing methods.

Furthermore, it is known in the art to determine SBn and In based on the Heithaeus p-value three dilutions procedure, whereby flocculation is measured on the pure stream containing asphaltenes (crude, residuum) and on the same sample diluted with an aromatic solvent (usually toluene). For example, this technique is generally described in U.S. Patent Publication No. 2013/0341241, published Dec. 26, 2013, and assigned to Baker Hughes Incorporated, the contents of which are incorporated by reference herein in their entirety.

However, the dilution makes the sample much more stable (more precipitant is needed, usually heptane) which makes the accurate determination of the flocculation onset very difficult or impossible, as the asphaltenes are extremely diluted at the flocculation onset many times.

This issue is avoided by the presently disclosed subject matter as the $SB_{feed}$ is measured directly on the process stream and the IN is measured as the RI at the flocculation onset. If the process stream is a solid at ambient temperature, it can be solvated with xylene and the RI measurement can be run on the diluted sample. As the presently disclosed method is able to accurately determine the flocculation onset of virtually any stream containing asphaltenes, the SBn and IN of a very wide range of streams can be measured.

The SBn and IN may be, in principle, determined by the three dilutions method, but this can fail sometimes or give wrong results. The basis of the experimental determination of the solubility parameters, SBn and IN, by the three dilutions method is based on the assumption that the dilution with aromatic solvent does not change the asphaltenes and their corresponding IN. If this is true, then the three dilutions plot is linear. This is a flawed assumption and there are typically different regression lines depending on the selected dilution and solvent range used to compensate for it. Consequently, the calculated SBn and IN depend upon the dilution range selected. A non-linear three dilutions plot is shown in FIG. 1 hereto.

The approximate estimate of the stability reserve of asphaltenes in crude oils provided by prior art techniques is based on the fact that SBn is determined with the RI and, on the assumption that on average, the asphaltenes insolubility number, IN, in crudes and residues before thermal cracking is 0.25. The SBn from RI measurements can be divided by 0.25 to get an estimate of the stability reserve. For thermally cracked streams, the IN value is drastically increased by the thermal cracking process in a way that depends on the severity of thermal cracking. Thus, the impact on IN is significant and needs to be better detected. In these cases unless there is a measurement of the IN value by independent techniques, an estimate on stability reserve cannot be given based solely on the RI.

According to the presently disclosed subject matter, the refractive index measurement alone, without any other measurement run on the asphaltenes containing feeds, can be utilized to measure the oil solubility parameter and calculate the solubility blending number starting from proprietary correlations based on experimental data. This gives an approximate estimate of the stability reserve of non thermally cracked asphaltene containing streams. If stability reserve is measured together with refractive index on the same stream, then the determination of the stability reserve becomes very accurate, and not simply an estimate, and can be extended to thermally cracked streams such as FCC slurries, H-Oil, LC Finer, Eni Slurry Technology EST unit and visbreakers.

While the disclosed subject matter has been described in detail in connection with a number of embodiments, it is not limited to such disclosed embodiments. Rather, the disclosed subject matter can be modified to incorporate any number of variations, alterations, substitutions or equivalent arrangements not heretofore described, but which are commensurate with the scope of the disclosed subject matter.

Additionally, while various embodiments of the disclosed subject matter have been described, it is to be understood that aspects of the disclosed subject matter may include only some of the described embodiments. Accordingly, the disclosed subject matter is not to be seen as limited by the foregoing description, but is only limited by the scope of the appended claims.

What is claimed is:

1. A method of controlling a crude oil refining process having a process stream containing asphaltenes, the method comprising:
deploying a refractive index probe at a location suitable for making a crude oil stability determination;
determining the solubility parameters and stability reserve of the crude oil; and
controlling the crude oil refining process by maintaining the process or implementing a change to the process based upon the determination of the solubility parameters and stability reserve, the step of determining comprising:
(a) determining the solubility parameters by measuring a refractive index of the process stream (RI) and the refractive index at a flocculation onset of the asphaltenes (RIo), wherein the flocculation onset is determined via turbidimetric titration, and wherein the measuring comprises:
(i) utilizing the refractive index parameters of the process stream (RI) as a direct measurement of a solubility blending number (SBo); and
(ii) utilizing the refractive index parameters at the flocculation onset of the asphaltenes (RIo) as a direct measurement of an insolubility number (IN);
(b) determining the stability reserve by calculating the stability reserve from the solubility blending number (SBo) and the insolubility number (IN);
(c) recovering precipitated asphaltenes at the flocculation onset, redispersing the precipitated asphaltenes in a solvent to form an asphaltenic solution, measuring the refractive index parameters of the asphaltenic solution (RIa), and converting the refractive index parameters (RIa) into a solubility blending number (SBa) of the precipitated asphaltenes;
(d) making a measurement of crude oil stability, wherein the difference in the solubility blending number of the oil and the IN measured from RIo at the asphaltenes flocculation onset ($SB_o$-IN) is indicative of the stabilizing/solvating role of one or more resins in the fluid on the asphaltenes; and
(e) making a measurement of the stabilizing/solvating role of the resins in the fluid on the asphaltenes, wherein the difference in the solubility blending number of the oil and the solubility parameter of the process stream with precipitant at the flocculation onset ($SB_a$-IN) is indicative of the stabilizing effect of the resins.

2. The method of claim 1, wherein the precipitated asphaltenes are recovered via one or more of filtration or centrifugation.

3. The method of claim 2, wherein the recovered precipitated asphaltenes are washed with precipitant and then recovered again via one or more of filtration or centrifugation.

4. The method of claim 1, wherein the precipitated asphaltenes are redispersed in the solvent at a ratio in the range from 1:1 solvent/asphaltenes to 10:1 solvent/asphaltenes.

5. The method of claim 1, wherein the process stream comprises one or more of light crude oil, heavy crude oil and a refinery stream comprising one or more of desalted crudes, vacuum tower bottoms, FCC slurries and heavy fuels.

6. The method of claim 1, wherein the process stream comprises a crude oil derivative from a refinery process.

7. The method of claim 1, wherein the process stream comprises a light crude oil with an asphaltenes content of 0.40% or greater.

8. The method of claim 1, wherein the process stream comprises a residual thermal cracking stream from a refinery process.

9. The method of claim 8, wherein the residual thermal cracking stream comprises one or more of an FCC slurry, an H-Oil, an LC Finer and a visbreaker.

10. The method of claim 1, wherein the process stream comprises a residual hydrocracking stream from a refinery process.

11. The method of claim 1, wherein the process stream comprises a refinery distillate stream containing no asphaltenes combined with a stream containing asphaltenes.

12. The method of claim 1, wherein the refractive index can be directly measured during turbidimetric titration using one or more of fiber optic, near infrared or refractometer coupled with the turbidimeter.

13. A method of transporting or storing crude oil containing asphaltenes comprising:
deploying a refractive index probe in a crude oil transportation or storage system;
making a determination of solubility parameters and stability reserve; and
controlling the process for transporting or storing the crude oil by maintaining the process or implementing a change to the process, based upon the determination of solubility parameters and stability reserve, wherein the determination comprises:
(a) determining the solubility parameters by measuring a refractive index of the process stream (RI) and the refractive index at a flocculation onset of the asphaltenes (RIo), wherein the flocculation onset is determined via turbidimetric titration, and wherein the measuring comprises:
(i) utilizing the refractive index parameters of the process stream (RI) as a direct measurement of a solubility blending number (SBo); and
(ii) utilizing the refractive index parameters at the flocculation onset of the asphaltenes (RIo) as a direct measurement of an insolubility number (IN);
(b) determining the stability reserve by calculating the stability reserve from the solubility blending number (SBo) and the insolubility number (IN);
(c) recovering precipitated asphaltenes at the flocculation onset, redispersing the precipitated asphaltenes in a solvent to form an asphaltenic solution, measuring the refractive index parameters of the asphaltenic solution (RIa), and converting the refractive index parameters (RIa) into a solubility blending number (SBa) of the precipitated asphaltenes;

(d) making a measurement of crude oil stability, wherein the difference in the solubility blending number of the oil and the IN measured from RIo at the asphaltenes flocculation onset (SBo-IN) is indicative of the stabilizing/solvating role of one or more resins in the crude oil on the asphaltenes; and (e) making a measurement of the stabilizing/solvating role of the resins in the crude oilfluid on the asphaltenes, wherein the difference in the solubility blending number of the oil and the solubility parameter of the process stream with precipitant at the flocculation onset (SBa-IN) is indicative of the stabilizing effect of the resins.

14. A method of optimizing a chemical program for a process stream containing asphaltenes, the method comprising:

deploying a refractive index probe at a location suitable for making a stability determination for the process stream;

determining the solubility parameters and stability reserve of the process stream; and adjusting the amount of a chemical additive to the process stream based upon the determination of the solubility parameters and stability reserve, the step of determining comprising:

(a) determining the solubility parameters by measuring a refractive index of the process stream (RI) and the refractive index at a flocculation onset of the asphaltenes (RIo), wherein the flocculation onset is determined via turbidimetric titration, and wherein the measuring comprises:

(i) utilizing the refractive index parameters of the process stream (RI) as a direct measurement of a solubility blending number (SBo); and (ii) utilizing the refractive index parameters at the flocculation onset of the asphaltenes (RIo) as a direct measurement of an insolubility number (IN);

(b) determining the stability reserve by calculating the stability reserve from the solubility blending number (SBo) and the insolubility number (IN);

(c) recovering precipitated asphaltenes at the flocculation onset, redispersing the precipitated asphaltenes in a solvent to form an asphaltenic solution, measuring the refractive index parameters of the asphaltenic solution (RIa), and converting the refractive index parameters (RIa) into a solubility blending number (SBa) of the precipitated asphaltenes;

(d) making a measurement of stability, wherein the difference in the solubility blending number and the IN measured from RIo at the asphaltenes flocculation onset ($SB_o$-IN) is indicative of the stabilizing/solvating role of one or more resins in the fluid on the asphaltenes; and (e) making a measurement of the stabilizing/solvating role of the resins in the fluid on the asphaltenes, wherein the difference in the solubility blending number and the solubility parameter of the process stream with precipitant at the flocculation onset ($SB_a$-IN) is indicative of the stabilizing effect of the resins.

* * * * *